(12) United States Patent
Soon-Shiong et al.

(10) Patent No.: US 11,881,315 B1
(45) Date of Patent: Jan. 23, 2024

(54) SENSOR-BASED LEADING INDICATORS IN A PERSONAL AREA NETWORK; SYSTEMS, METHODS, AND APPARATUS

(71) Applicant: Nant Holdings IP, LLC, Culver City, CA (US)

(72) Inventors: Patrick Soon-Shiong, Los Angeles, CA (US); Nicholas J. Witchey, Laguna Hills, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

(21) Appl. No.: 17/888,456

(22) Filed: Aug. 15, 2022

(51) Int. Cl.
| | | |
|---|---|---|
| *G16H 50/30* | (2018.01) | |
| *G16H 50/70* | (2018.01) | |
| *G16H 40/67* | (2018.01) | |
| *A61B 5/00* | (2006.01) | |

(52) U.S. Cl.
CPC ........... *G16H 50/30* (2018.01); *A61B 5/0024* (2013.01); *G16H 40/67* (2018.01); *G16H 50/70* (2018.01)

(58) Field of Classification Search
CPC ........ G16H 50/30; G16H 40/67; G16H 50/70; A61B 5/0024
See application file for complete search history.

(56) References Cited

U.S. PATENT DOCUMENTS

| | | |
|---|---|---|
| 10,218,732 B2 | 2/2019 | Wittenschlaeger |
| 10,296,840 B2 | 5/2019 | Soon-Shiong |
| 10,340,038 B2 | 7/2019 | Witchey |
| 10,667,212 B2 | 5/2020 | Chaturvedi et al. |
| 10,762,171 B2 | 9/2020 | Dyell et al. |
| 11,017,884 B2 | 5/2021 | Soon-Shiong |
| 11,017,897 B2 | 5/2021 | Soon-Shiong |
| 11,403,795 B2 | 8/2022 | Moore et al. |
| 2017/0034023 A1* | 2/2017 | Nickolov ............ H04L 43/0817 |
| 2017/0094355 A1* | 3/2017 | McCarty ............... G06F 16/735 |
| 2018/0039731 A1 | 2/2018 | Szeto |
| 2018/0247713 A1* | 8/2018 | Rothman ........... A61B 5/02055 |
| 2018/0342106 A1* | 11/2018 | Rosado ................ G06Q 10/109 |
| 2019/0209022 A1* | 7/2019 | Sobol ................... A61B 5/0022 |
| 2019/0268612 A1* | 8/2019 | Fukuyasu ............ H04N 21/234 |
| 2020/0236278 A1* | 7/2020 | Yeung ................ H04N 21/2187 |

(Continued)

OTHER PUBLICATIONS

U.S. Appl. No. 17/590,291 to Witchey et al. titled "Token-Based Digital Private Data Exchange Systems, Methods, and Apparatus," filed Feb. 1, 2022.

*Primary Examiner* — Jay M. Patel
(74) *Attorney, Agent, or Firm* — Mauriel Kapouytian Woods LLP; Andrew A. Noble

(57) ABSTRACT

A sensor-based leading indicator management ecosystem is described. Sensor data associated with the individual, possibly within a Personal Area Network (PAN) and related to the healthcare of the individual, is compiled and converted to a one or more sets of leading indicators with respect to one or more possible future healthcare actions. Leading indicators may then be compiled into one or more condition state vectors that represent encoded inputs into one or more trained action prediction agents. The trained action prediction agents then generate, possibly in real-time or based on time-series data, predicted actions that may be required at a predicted point-of-care or a moment-of-care. Further, action prediction agents may be context or domain specific.

37 Claims, 5 Drawing Sheets

(56) References Cited

U.S. PATENT DOCUMENTS

| | | | | |
|---|---|---|---|---|
| 2021/0319894 A1* | 10/2021 | Sobol | ........................ | G06N 7/01 |
| 2021/0375468 A1* | 12/2021 | Zhang | ................... | A61B 5/7267 |
| 2021/0407667 A1* | 12/2021 | Zhi | ........................ | G16H 50/20 |

* cited by examiner

US 11,881,315 B1

SENSOR-BASED LEADING INDICATORS IN A PERSONAL AREA NETWORK; SYSTEMS, METHODS, AND APPARATUS

FIELD OF THE INVENTION

The field of the invention is technologies related to sensor-based, personal area networks.

BACKGROUND

The background description includes information that may be useful in understanding the present inventive subject matter. It is not an admission that any of the information provided herein is prior art or applicant admitted prior art, or relevant to the presently claimed inventive subject matter, or that any publication specifically or implicitly referenced is prior art or applicant admitted prior art.

As healthcare and fitness technologies have grown, the use of personal sensors has grown as well. Sensor data collected from an individual's personal area network can be used to aid stakeholders to determine if the individual is healthy or is suffering from a severe condition. However, sensor data, even real-time sensor data, often lag critical events such as a heart attack. Thus, even when an individual is close to a point-of-care and the sensor data is obtained in real-time, treatment of a detected condition may come too late especially when every second counts.

Progress has been made in sensor-based technologies and corresponding reporting technologies. For example, in a hospital setting the Philips® Patient Information Center iX system provides a patient monitoring system capable of displaying vital signs for multiple patients at the same time to multiple stakeholders. If one or more events are sensed, the system generates an appropriate alert. While useful in a hospital, such systems do not address the need for remote monitoring in a non-care related setting. Further progress has been made by the AirStrip ONE® technology capable of displaying sensed waveforms or medical images on a cell phone thereby fulfilling, at least partially, the need for remote monitoring. Additionally, from a sensor standpoint, remote data collection has become easier via multi-parameter wearable sensors such as the BioIntellisense® BioSticker™ or BioButton™ sensors, which are capable of capturing temperature, resting heart rate, respiratory rate, gait analysis and body position.

Even in view of the progress made in sensor-based monitoring, identification of important events from the sensor data still may result in a lagging response to the identified important events, which could be significant in situations where the individual is distant from a point-of-care. A more ideal approach, as discussed below with respect to the disclosed inventive subject matter, would leverage sensor data or other data related to the individual to identify leading indicators for important events and then predict a required action. Further such predictions can include predictions of when or where such actions would be needed, which does not exist in the existing technologies discussed above.

Thus, there is still a need for systems, methods, or apparatus by which a sensor data can be converted to a predicted required action to address a change in an individual's circumstance.

SUMMARY

The inventive subject matter provides apparatus, systems and methods in which sensor data from at least a personal area network (PAN) is collected and analyzed in order to predict an action at a point-of-care, a time-of-care, a moment-of-care, or other care-related parameter. In some embodiments the inventive subject matter comprises a PAN that includes a set of one or more sensors and a sensor hub. The set of sensors are capable of capturing sensor data associated with an individual. For example, the set of sensors could capture digital data representing vital signs (e.g., heart rate, blood pressure, respiration, skin galvanic response, oxygen, etc.) of an athlete during a training session or during a competition. The sensor hub can be considered a computing device with a computer readable memory and at least one processor. The sensor hub couples with the set of sensors, possibly via a wireless communication channel or wired channels in the PAN. Upon the processor of the hub executing software instructions stored in the memory, the sensor hub is enabled to perform multiple operations including obtaining at least one action prediction agent and storing the agent in the memory. The action prediction agents may include a digital implementation of a trained machine learning model that accepts a condition state vector (e.g., formatted leading indicators of the individual, etc.) as input and then generates at least one predicted action that the individual may be in need thereof at a point-of-care or a time-of-care. The operations may further include generating, preferably in real time, a set of leading indicators from the sensor data. Further, the operations can also include forming a condition state vector from the leading indicators in a manner where the condition state vector is formatted or otherwise presented in an acceptable digital format for consumption by the action prediction agent. Continuing with the operations, the hub may generate one or more predicted actions for a possible condition of the individual based on the condition state vector. More specifically, the prediction actions could include an action to be taken by the individual, a stakeholder (e.g., doctor, trainer, etc.), a device, or other entity to address the possible condition. In some scenarios, the predicted action may be generated relative to a known state of the individual (e.g., relative to a resting state, relative to an exertion state, etc.). In view the sensor hub may be part of a PAN, the operations may also include causing a computing device, possibly a remote device, to render the predicted required action, where an alert with the predicted required action may be transmitted over a network to the output computing device.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
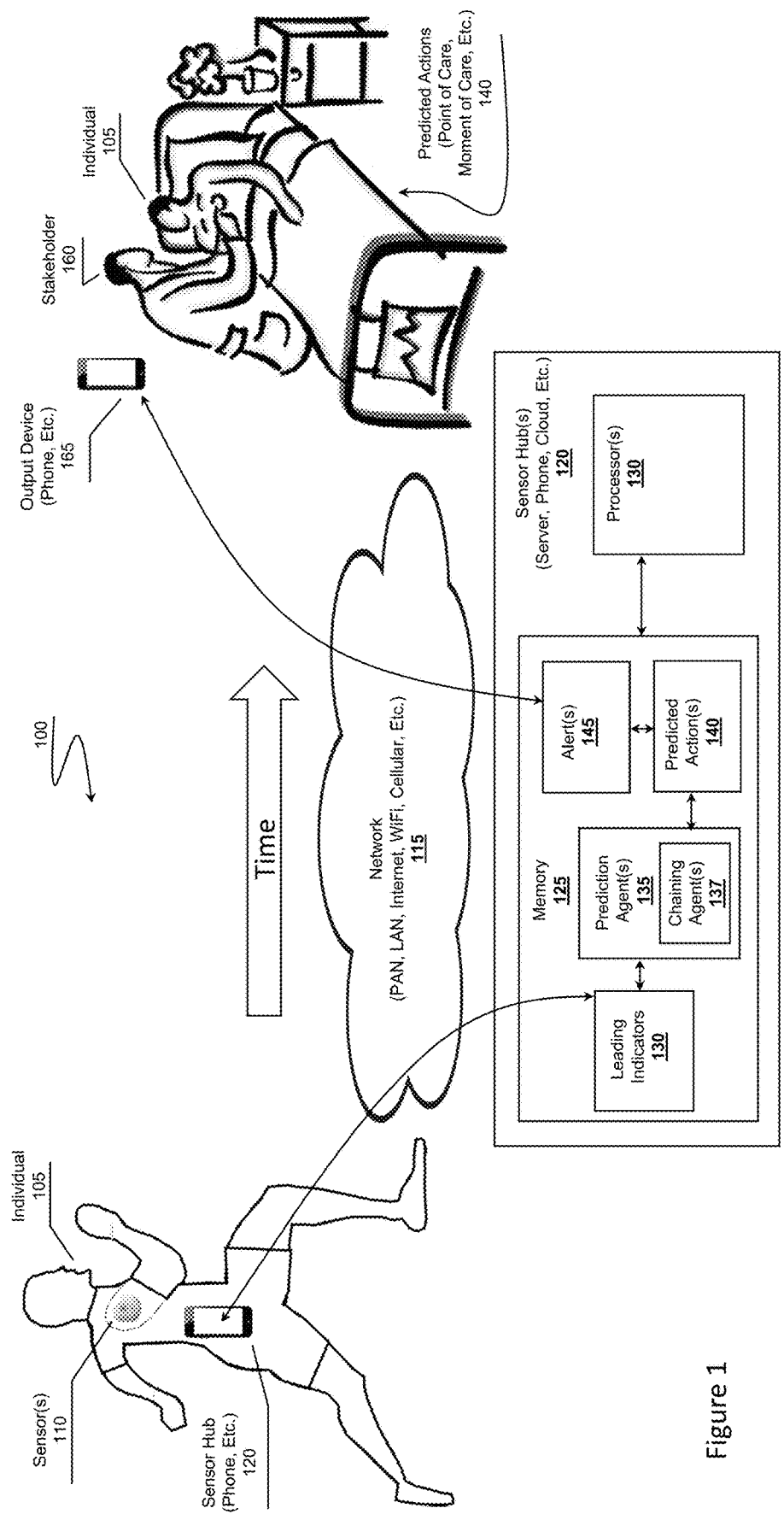
FIG. 1 is an overview of a personal area network (PAN) where sensor data is used to identify leading indicators for a point-of-care.

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed below with respect to the disclosed apparatus(es). Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of communication network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

One should appreciate that the disclosed techniques provide many advantageous technical effects including processing multi-modal digital sensor data and executing digital implementations of machine learning algorithms on the sensor data, which are able to generate a predicted action quickly in near real-time. As discussed below, the disclosed techniques also account for establishing machine learning prediction agents that are sensitive to the limitations of computing devices by ensuring the agents are able to operate in environments having limited memory or limited computational power. Thus, devices employing the disclosed techniques are able to quickly convert sensor data into device actions via leading indicators. For example, upon quickly detecting a set of leading indicators and generating a set of predicted required actions, the set of predicted required actions can be efficiently packaged into an alert and transmitted over a network preferably before an important event occurs.

The focus of the disclosed inventive subject matter is to enable construction or configuration of a computing device to operate on vast quantities of digital data, beyond the capabilities of a human. Although the digital data represents a condition or state of an individual, it should be appreciated that the digital data is a representation of one or more digital models of the condition, not the actual condition itself. By instantiation of such digital models, including trained machine learning models, in the memory of the computing devices, the computing devices are able to manage the digital data or models in a manner that could provide utility to a user of the computing device that the user would lack without such a tool.

The following subject matter is presented from a healthcare perspective where an individual may be a patient or a person that may need care. However, there are other use cases beyond healthcare that could benefit from the disclosed techniques. For example, the disclosed machine learning systems and personal area networks (PANs) could be leveraged for sports, military uses, automotive repair, or athletics, to name a few.

FIG. 1 presents an overview of the inventive subject matter from the perspective of healthcare ecosystem 100 where individual 105 might need care at a future time. At a first point in time, individual 105 is being monitored via a set of sensors 110 connected to sensor hub 120, which are members of a PAN disposed in or about individual 105. Sensors 110 can include one or more sensor, which can collect a broad spectrum of digital data modalities. Example sensors can include heart rate sensors, respiration sensors, pulse-ox sensors, location sensors (e.g., GPS, wireless triangulation, etc.), cameras (e.g., CCD, CMOS, etc.), microphones, infrared sensors, galvanic response sensors, capacitance sensors, resistance sensors, temperature sensors, accelerometers, magnetometers, gyroscopes, or other types of sensors. In more preferred embodiments, the sensor data collected from sensors 110 pertain to individual 105. Still, it is possible the example use case in FIG. 1 could be extended to cover a group of individuals or other type of cohort. While individual 105 is illustrated as a human being, individual 105 could be non-human and might include animals or plants. In which case, sensors 110 might comprise other types of sensors for the target type of individual. Additionally, individual 105 might also include a machine (e.g., plane, automobile, appliance, robot, computer, etc.). However, as stated previously, the discussion regarding the inventive subject matter will continue to focus on a healthcare environment for a human for illustrative purposes without narrowing the scope of the inventive subject matter.

Sensor hub 120, typically operating on or as a smart phone, is a computing device having at least one of processors 130 and at least one computer readable memory 125. For example, sensor hub 120 can be a cell phone located on individual 105 and can participate as an active member of the PAN. Still, sensor hub 120 could be deployed as a server or as a cloud instance possibly located over network 115 (e.g., LAN, WAN, Internet, etc.) where the server or cloud instance is communicatively coupled with the PAN. In more preferred scenarios, sensor hub 120 comprises a cell phone or other personal device (e.g., smart watch, PDA, tablet, gaming device, etc.) provisioned with one or more of prediction agents 135 and operates locally within a PAN on sensor data collected from sensors 110. Example PANs that may be adapted for use with the inventive subject matter includes those described in U.S. Pat. No. 10,667,212 to Chaturvedi et al. titled "Power Management of a Personal Area Fabric," filed Oct. 14, 2019.

Sensor hub 120 gathers or compiles sensor data from sensors 110 and converts the sensor data to one or more leading indicators 130. Leading indicators 130 comprise a set of sensed or otherwise measured values relating to the individual and that may be indicative of one or more possible or potential conditions that may arise at a future time. Still, leading indicator 130 could comprise raw sensor data, a temperature value for example. However, leading indicators 130 could also comprise derived values from the sensor data. In some embodiments, a sensor might only provide a raw value of 0 to 255, for example, which is then converted to a corresponding leading indicator measure possibly via a function, via a look-up table, or other digitally implemented transformation. Still further leading indicators 130 are not required to have a one-to-one mapping to sensor data modalities. In some embodiments, a single leading indicator value could represent a measured value derived from more than one sensed value from the sensor data. Consider an example where individual 105 is jogging. The accelerometry data (i.e., movement) coupled with a high heart rate and a higher temperature all together might map to a nominal activity. However, the same set of data modalities (e.g., no movement, high heart rate and high temperature) might be a solid leading indicator of a possible issue. Thus, an individual leading indicator 130 can be a value derived from many sensor data feeds, possibly based on a context of an individual and according to one or more leading indicator rules sets.

Leading indicators 130 may be generated or otherwise instantiated according to one or more rules set, which may be included with or in prediction agent 135. Prediction agent 135, in some embodiments, typically comprises one or more trained machine learning models that accept an input vector, referred to below as a condition state vector, of leading indicators 130. Examples of prediction agents 135 can include neural networks, classifiers, regression models, or other implementations of machine learning algorithms. Sources for machine learning algorithms include OpenCV for computer vision (see URL opencv.org), SciKit Learn (see URL scikit-learn.org), TensorFlow (see URL tensorflow.org), and Keras (see URL github.com/keras-team/keras) that runs on top of TensorFlow, just to name a few.

Prediction agent 135 executes corresponding software instructions by which leading indicators 130 are converted or transformed into one or more of predicted actions 140. Once leading indicators 130 are compiled into corresponding input vectors (i.e., condition state vectors) for prediction agent 135, prediction agents 135 generate corresponding predicted actions 140. Predicted actions 140 can take on a broad spectrum of possible predicted outcomes. In view that leading indicators 130 are indicators of one or more future condition, prediction actions 140 can include a predicted time as a predicted moment-of-care when a need for care might arise for a condition that might occur or be present. Further, in some embodiments, leading indicators 130 can include additional factors beyond those related to the health for individual 105. For example, leading indicators 130 could include GPS information or movement information related to the individual. In which case, predicted actions 140 can comprise a predicted point-of-care as a predicted location based on movement of individual 105.

In some embodiments, prediction agent 135 could also comprise one or more chaining agents 137. Chaining agents 137 comprises software instructions that execute implementations of one or more rules sets that extrapolate, when necessary, a plan of action. Chaining agents 137 may be necessary under conditions where a predicted action might not be practical due to context or environmental issues. For example, a skilled healthcare provider might not be in proximity to provide care according to a predicted action, say providing stitches as an example. In such cases, the chaining agent 137 receives the predictions from the prediction agent 135 as input and executes one or more chaining rules (i.e., rules encoded in the software instructions) to determine what can be done from a practical sense in a practical amount of time. To continue the example, bystanders could be notified to stop bleeding via pressure while the skilled healthcare provider arrives. In addition to or alternatively, if no one is available, the resulting practical action plan might include an action to provide blood as soon as possible.

When one or more predicted actions 140 satisfy triggering criteria, sensor hub 120 can generate one or more of alerts 145. Alerts 145 may be packaged by sensor hub 120 based on the information provided from individual 105, leading indicators 130, prediction agents 135, prediction actions 140, or other related information as desired. Consider an example where a runner is in a long-distance race. During the race prediction agent 140 may generate numerous calls to action, but none might rise to a level of criticality. However, as time passes, a moisture sensor and heart rate sensor provide data, in combination, that indicates the runner will become too dehydrated shortly, say in 10 to 15 minutes. The predicted action 140 may comprise actions including instructions for providing water within 10 minutes. The corresponding alert 145 could include the following information: an identifier associated with individual 105 (e.g., name, competitor number, etc.), a predicted location (e.g., coordinates, street intersection, rest stop, etc.) where water should be supplied based on the individual's movement, an amount of water or hydrant to supply, stakeholders to notify (e.g., coach, physician, race official, family members, etc.), an identification of triggering criteria causing the alert, raw sensor data, or other information. This example illustrates several points. First, alert 145 can be triggered based on predicted actions 140 and based on other information available related to individual 105. Second, alert 145 can be packaged with a wide variety of information. Third, the predictions can include a location or time of care.

Alert 145 can be transmitted from sensor hub 120 over network 115 to one or more other devices as represented by output device 165. In the example shown, output device 165 is illustrated as a cell phone associated with stakeholder 160, a physician for example. However, it should be appreciated that stakeholder 160 could be other types of entities besides a physician. For example, stakeholder 160 could be individual 105, a family member of individual 105, a co-worker, a nurse, a coach, a military leader, an expert system or other computing device, or other entity that, preferably, can take action based on the predicted actions 140 packaged in alert 145. Further, although output device 165 is shown as a smart phone, output device 165 can be any practical computing device possibly including a desktop computer, smart watch, patient monitoring system, tablet, medical equipment, robot, vehicle, set top box, appliance, game console, or other device capable of rendering suggested actions.

By receiving one or more of alerts 145, stakeholder 160 is enabled to take action, which typically would include taking one or more of the predicted actions 140. However, it is possible stakeholder 160 may override the predicted action based on local information and context (e.g., at the specific engagement point in time, at the specific location, based on local equipment available for care, etc.). Still, stakeholder 160 can consult the information in alert 145 to determine what circumstances gave rise to the predicted actions. Additionally, stakeholder 160 can submit one or more queries back to sensor hub 120 to obtain additional information regarding individual. Assuming authorization is granted, sensor hub 120 can respond to the query with a result set or indicate where desired information could be found (e.g., remote healthcare database, etc.).

In some embodiments, such information may be stored in an intermediary database (not shown) between sensor hub and output device 165. For example, sensor hub 120 could send any desired information to the intermediary database along with corresponding alert identifiers. The information sent to the database can be inclusive of the alert information or could extend beyond the information in the alert including information preceding or postdating alert 145 so that stakeholder 160 could have access to a broader scope or context of the predicted actions 140. Use of such an intermediary database is considered advantageous in cases where sensor hub 120 has reduced storage capacity in memory 125. In particularly interesting embodiments, alerts 145 and associated information can be stored on or associated with a blockchain or other form of notarized or distributed ledger. Storing alert 145 on such notarized ledgers provides for auditing the data at a future time, possibly for machine learning tasks to support the ecosystem or for insurance purposes.

Figure 2:
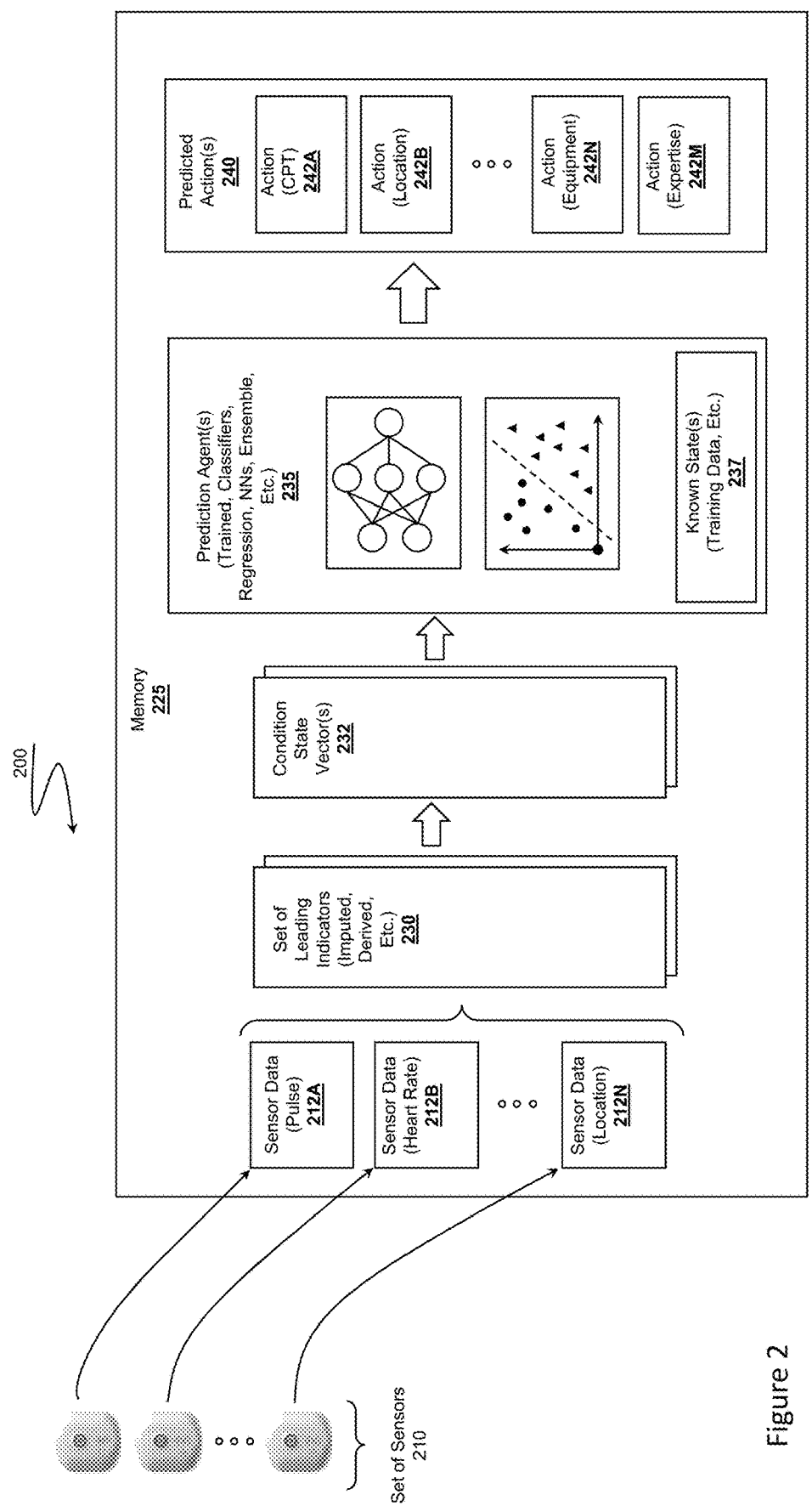
FIG. 2 presents an example of a sensor hub in a PAN that generates a predicted action.

FIG. 2 presents memory management ecosystem 200 that includes additional details regarding the flow of data through memory 225, which may operate as part of a sensor hub. Memory 225 is presented from a generic perspective. However, one should appreciate the features of memory 225 could be deployed in one or more devices including purpose-built or dedicated devices. Consider, for example, an embodiment where the inventive subject may be packaged for specific use cases (e.g., domain specific, context specific, etc.). A use-case package can comprise one or more executable code and data structure compilations. In such cases, the package can include the use-case specific rules for compiling leading indicators from sensor data, rules and code for converting the leading indicators into the condition state vector, and prediction agents specifically trained for the use case. Still, one should appreciate that more than one prediction package may be active at the same time. For example, an athlete might have a healthcare package that is active and making predictions at an end-of-game point in time while also having a physical therapy package active for long term care and yet a third package focused on real-time injuries during a game. Further the package can include the use case specific rules for routing corresponding alerts or notifications to one or more appropriate stakeholders. Still further, each use case specific package could be installed on the same device or on different devices. Continuing with the athlete example, the packages could be installed on a cell phone, say for a runner, or in a helmet-installed device for a baseball player or American football player.

In the example shown in FIG. 2, the set of sensors 210 can include one or more sensors that can include a variety of sensors as discussed above. Set of sensors 210 can produce a variety of sensor data as represented by sensor data 212A through 212N, collectively referred to as sensor data 212. Thus, sensor data 212 can comprise a broad spectrum of data modalities. For example, sensor data 212A can include pulse data obtained from an individual, sensor data 212B can include heart rate data from the individual, and sensor data 212N can comprise location data (e.g., GPS coordinate, zip code, address, Google Plus code, etc.) related to the individual.

While sensor data 212 is presented as discrete objects in memory 225, it should be appreciated sensor data 212 can be managed via one or more techniques. In some scenarios, sensor data 212 can comprise one or more data streams that includes data values streaming from the corresponding sensor in set of sensors 210. Typically, sensor data streams can be represented as time series data in memory 225. Sensor data streams can be managed individually or collectively as instantiated data stream class objects in embodiments leveraging object-oriented programming languages. In addition to or alternatively to sensor data streams, sensor data 212 can be represented as sensed values stored in appropriate data structures. Such an approach is useful for data that does not vary substantially in time (e.g., body weight, ethnicity, etc.). Further, streamed or not, sensor data 212 can be obtained from set of sensors 210 through various techniques, possibly over the PAN, including the sensor hub pulling the data from set of sensors 210, receiving pushed data from set of sensors 210, receiving updated sensor data via registers or electrical inputs (e.g., programmable I/O pins, wired interfaces, etc.), or other methods.

Sensor data 212 can include raw sensor data or derived sensor data. Raw sensor data can be considered as representing the direct output from the corresponding sensor, where the values of the sensor data might be in the final form (e.g., a temperature, a pulse, etc.) or might be an intermediary value (e.g., integer from 0 to 255, etc.) that might need further processing. For example, if the raw sensor data is an analog value, the analog value might require conversion to a digital value via a A-to-D converter. The digital value may need further conversion by the sensor hub to a final measured value. Thus, it should be appreciated sensor data 212 can comprise raw binary data, text data, data with corresponding measurement units, or other forms.

Sensor data 212 can also be domain specific depending on the nature of the target use case of the inventive subject matter. While the present disclosure focuses mainly on the illustrative example of healthcare where the set of sensors 210 would typically collect health signs, it is possible that other packages of sensors could collect other types of sensor data 212. For example, in military use cases, set of sensors 210 could include sensors related to personal logistics (e.g., ammunition, food, etc.) or other information. Therefore, it is contemplated that a package of sensors could be created for target use cases to supply the sensor hub with corresponding domain-specific sensor data 212. Such a package of sensors may be part of a larger package of hardware, software, or other elements for specific domains or applications. For example, larger domain-specific packages may service markets including sports, athletics, health care, physical therapy, training, entertainment, or other markets.

As sensor data 212 flows through the system, it can be transformed into set of leading indicators 230. Set of leading indicators 230 can comprise one or more leading indicator objects created according the rules encoded in the software instructions. As discussed above, the leading indicators could be actual data from sensor data 212, derived from sensor data 212, or otherwise imputed from sensor data 212. In some scenarios there may be a one-to-one correspondence between values from sensor data 212 and a corresponding leading indicator, while in other scenarios there may be a many-to-one or even many-to-many relationship between sensor data values and the leading indicators. One should appreciate in view of leading indicators are "leading," there are temporal relationships that may need to be incorporated. While a person's weight (a possible leading indicator) might not change quickly, other leading indicators may change relatively quickly; heart rate, respiration, or oxygen level just as examples. Therefore, in some embodiments, a leading indicator in set of leading indicators 230 may be stored in memory 225 as a time series data structure that captures how corresponding sensor data values or their derived values change with time. This approach is considered advantageous because it allows for making predictions based on a trend of a leading indicator in time or based on a set of trends among multiple leading indicators.

At any moment in time, it is possible that more than one prediction agent may be active. To support more than one prediction agent, memory 225 may be storing more than one set of leading indicators 230. More specifically, memory 225 may store many sets of leading indicators 230 where each set could support a specific prediction activity. Still, it is possible that set of leading indicators 230 could be a single comprehensive pool of leading indicators from which active prediction agents may draw activity-specific leading indicators for a specific task. Thus, the management of set of leading indicators 230 may be performed in parallel with many other sets.

Set of leading indicators 230 is used as an input to create or otherwise instantiate one or more of condition state vector 232, which represents the actual data structure input to prediction agents 235. As alluded to above, at any given time one or more prediction task may be active. Therefore, more than one condition state vector 232 may be compiled to service a corresponding prediction task. Further, while each conditions state vector 232 may be different, they may be compiled from the same set of leading indicators 230. Still further, condition state vector 232 may be compiled or instantiated based on time; every second, every 10 seconds, continuously, based on triggers, or based on other factors related to time. Such an approach is considered very advantageous in embodiments where time series data (e.g., EKGs, waveforms, respiration, heart rate, movement, etc.) is more critical.

Leading indicators can take on a broad spectrum of information that can then be fed into condition state vector 232. For example, leading indicators can be measured relative to a base-line or nominal value. As the average value changes for a given time period, the updated average value may then be the leading indicator or give rise to a derived leading indicator. Further, it should be appreciated that such leading indicators based on statistical data can be based on other features beyond an average or mean, possibly including a mode, median, standard deviations, or other higher order moments. In some embodiments, leading indicators may be derived from measured waveforms as referenced above. In such cases set of leading indicators 232 can include values or other observations relative to individual waveforms or collections of waveforms (e.g., time series of waveforms, overlapping waveforms, etc.). Example techniques for managing wave forms are described in U.S. patent application publication 2013/0271469 to Moore et al. titled "Systems and Methods for Collecting and Viewing Patient Data," filed Apr. 15, 2013. More specifically waveforms can be collected as a function of time and compared to a known nominal waveform or compared to a rolling average in order to generate leading indicators, possibly where the calipers described in U.S. patent application publication 2013/0271469 may be generated automatically or determined based on observed behaviors of the individual or context.

The software instructions associated with the prediction task can include one or more rules (e.g., functions, methods, etc.) by which condition state vector 232 is constructed. For example, in some cases condition state vector 232 could comprise a one-dimensional vector of integer values, where each value may be pulled from set of leading indicators 230 and represent a sensed state of the individual (e.g., heart rate, blood pressure, temperature, etc.). Additionally or alternatively, condition state vector 232 could comprise a two-dimensional array of values, where one dimension represents time (e.g., time stamps, etc.) and another dimension representing values measured at the corresponding times. Still, condition state vector 232 could comprise any practical number of dimensions for the target use case, domain-specific use, or for a given context. This approach provides for including a historical context of a current set of values. Thus, as each unit of time passes, the oldest values in the array may be discarded and the newest values may be added. In still other embodiments, condition state vector 232 may include padding or other forms of encoding.

Yet another type of encoding that can be leveraged with respect to condition state vector 232 includes a binary representation of sensed events. In such cases, set of leading indicators 230 might include a set of conditions or criteria defining an event. If the values in set of leading indicators 230 satisfy the event criteria, the corresponding value in condition state vector 232 can be set to "1" for TRUE or "0" for FALSE. While this example presents a binary condition, one should appreciate that other non-binary values could also be used; say NULL for the event is not present or used, or a numerical value indicating a degree to which the events criteria is satisfied (e.g., a Hamming distance, etc.).

Condition state vector 232 can also represent a delta from a nominal state rather than measure of the current absolute state at a point in time. The nominal state of an individual can be measured over time to build a representation or model of what might be considered "normal" or a baseline for the individual. In such embodiments, condition state vector 232 can be a set of differences between the baseline and the current state of the individual. This approach is considered advantageous because it provides for creating highly personalized or application-specific prediction tasks. For example, two athletes might have different baseline values, but their leading indicators could be the same for a given sporting event. Said differently, one individual's critical state could be another individual's normal state. Example techniques that may be leveraged to identify anomalous behaviors are described in U.S. Pat. No. 10,218,732 to Wittenschlaeger titled "Vector-Based Anomaly Detection," filed Apr. 6, 2017. While this patent focuses on digital network communications, the technique can also be adapted to establishing anomalous deviations from a baseline to give rise to leading indicators or to condition state vector 232.

Condition state vector 232, once compiled, can be provided to one or more of prediction agent 235. Prediction agent 235 are instantiated in memory 225 in order to fulfill desired prediction tasks. Prediction agents 235 can include digital implementations of machine learning models (e.g., neural networks, classifier, regression models, etc.) trained on one or more leading indicator training data sets. In the example shown, known states 237 can be considered to represent one or more training data sets used to train corresponding instantiated machine learning models. Further, known states 237 can also include a nominal or baseline state as discussed above from which predictions are made based on current sensor data 212. Examples of acceptable prediction agents 235 can include support vector machines (SVMs), random forests, artificial neural networks, nearest neighbors, and k-means clustering just to name a few. Sources for suitable implementations of machine learning algorithms include SciKit-Learn (see URL scikit-learn.org/ stable/), the TensorFlow platform (see URL tensorflow.org), and the Keras deep learning framework (see URL keras.io), which leverages TensorFlow. In view that sensor data 212 may include time-series data, in more interesting embodiments the implementations of machine learning models may include Long Short-Term Memory (LSTM) models, recurrent neural networks, gated recurrent network models, or multi-layer perceptron models to thereby leverage time-based information.

Based on the condition state vector 232 inputs, prediction agents 235 generate one or more predicted actions 240. Predicted actions 240 can be quite varied and depend on a specific use-case, domain, or context. However, predicted actions 240 typically include recommended or specific actions that should be taken at a predicted point of care or predicted moment of care at some point in the near future (e.g., in 5 minutes, in 10 minutes, in 1 hour, in 10 hours, in the next day, in the next week, etc.). One should appreciate prediction actions 240 depend on how prediction agents 235 have been trained on leading indicators. However, predicted locations of point of care or moment of care might not be easily generated from just health sensors. In such cases, additional information from the specific context may be used to generate or infer refinements regarding where or when an action should take place. Example context information that can be folded into making such predictions can include location (e.g., GPS coordinates, etc.), time stamps, user preferences, movements (e.g., speed, acceleration, higher order derivatives, etc.), information about care providers, insurance information, or other information. In some embodiments, a predicted action 240 might not be practical due to specific circumstances and, as discussed previously, one or more chaining agents may be used to establish a final practical predicted action. Of particular note, higher order derivatives can be calculated or otherwise derived based on differences in time or differences in other parameters. Thus, the higher order derivatives can include derivatives based on time (e.g., $d^2x/dt^2$, $d^4x/dt^4$, etc.) or even derivatives based on one parameter relative to another (e.g., $d^2x/dy^2$, $d^3x/dy^3$, $d^4x/dy^4$, etc.) where x and y represent observable parameters. For example, x might represent heart rate while y might represent respiration rate. While such derivative information can be used for context, the derivatives can also be used as leading indicators, used to generate leading indicators or even used in generating condition state vectors.

Predicted actions 240 can further include a broad spectrum of information about what action or actions should be taken. For example, as illustrated, predicted action 240 can include information such as Current Procedural Terminology (CPT) codes as represented by action 242A. CPT codes provide several advantages. First, by providing CPT codes, a care provider can know specifically and with certainty which procedure to perform. Second, providing one or more CPT codes allows for pre-adjudication by an insurance company if sufficient time is available. Third, CPT codes also provide a foundation for chaining prediction action together based on the interrelationship among coded procedures.

Other types of action information that can be included in prediction actions include location information, as discussed above and represented by action 242B, which can direct potential care givers to a point of care. Further, action information can include necessary equipment as represented by action 242N to support associated actions by care givers. Equipment information may include indications if the corresponding equipment may be required, optional, or just supporting in nature. Example equipment could include monitoring devices, surgical devices, triage equipment, emergency equipment, blood, splints, bandages, or other types of equipment or even materials. One should appreciate that the nature of the equipment can be quite varied. Still further, action information can include expertise, see action 242M, that may be needed or required at the point of care. Example expertise could represent the skills of stakeholders including specialists, doctors, nurses, paramedics, assistants, coaches, physical therapists, or other types of care providers. In such cases, the expertise can be coupled with specific recommendations on individuals that can fulfill such roles (e.g., family physician, local doctors, national experts, etc.).

In some embodiments, prediction agents 235 can operate as an ensemble of trained machine learning models, where the ensemble includes multiple implementation of different types of machine learning algorithms (e.g., LTSM, RNN, SVMs, random forests, etc.). The advantage of such an approach is that having multiple types of models analyzing the same input data aids in reducing potential bias (e.g., possibly training biased inadvertently introduced during training). Thus, the complete ensemble of models would generate many possible prediction actions 240, which can be overlapping or not overlapping. Therefore, prediction actions 240 can comprise a ranked listing of generated actions where the generated actions can be ranked based on how many models "voted" for the action, normalized certainty for the actions based on confidence levels of the prediction, normalized probabilities based on statistics of the prediction actions, or based on other factors. Example ensemble techniques that could be adapted for use with the disclosed inventive subject matter includes those described in U.S. patent application publication 2018/0039731 to Szeto titled "Ensemble-Based Research Recommendations Systems and Methods" filed Sep. 1, 2017.

Figure 3:
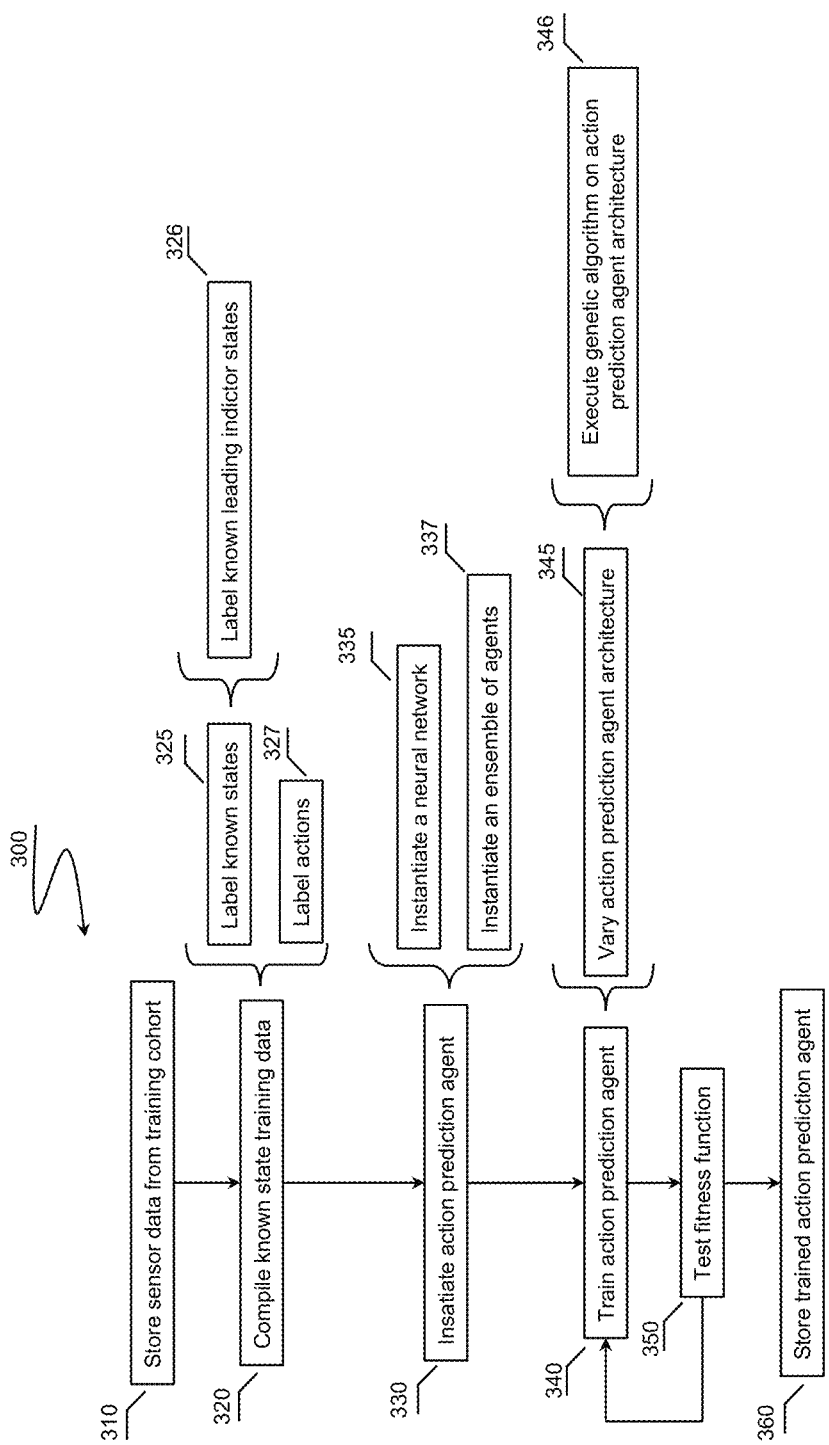
FIG. 3 illustrates a method of training an action prediction agent.

FIG. 3 presents computer-implemented method 300 of training one or more prediction agents. As referenced above, the trained prediction agents may be generic in nature or could be application specific (e.g., domain specific, context specific, use-case specific, etc.). For example, prediction agents could be trained on a broad spectrum of possible healthcare needs for general purpose use. Such an approach may be advantageous when monitoring an otherwise healthy individual. Still, prediction agents can be trained for use-cases such as physical therapy, athletic training, sports, or other specific cases where the types of care might be limited to the specific uses. Consider an example of a football player being monitored during a professional game. The football player could be provisioned with the trained prediction agent trained to observe leading indicators for concussion (e.g., head trauma, erratic gate, etc.). However, a person who is not an athlete during the day might not necessarily need a trained prediction agent to predict concussions as such a prediction might be a low probability. While prediction agents trained for general use might seem best, it should be appreciated that sensor hubs might have limited memory or computational power. Therefore, a tradeoff between breadth of training coverage and computational resources may be necessary.

Step 310 includes storing sensor data from a training cohort, where the sensor data is stored in a computer-readable memory. The training cohort could be based on a general population, a specific population (e.g., specific demographics, specific psychographics, etc.), a group of people, a group of animals, or other type of cohort. For example, the training cohort could be defined based on one or more attributes (e.g., location, age, ethnicity, profession, hobbies, diet, etc.). More specifically, as an example, a cohort could comprise cancer survivors having received a specific immunotherapy and are between the ages of 55 and 75. Alternatively, a cohort could comprise young adults, male and female from ages 18 to 30, a cohort could comprise types of specific athletes (e.g., football players, track and field athletes, baseball players, basketball players, soccer players, golfers, etc.), or a cohort could even comprise animals. Thus, it should be appreciated the inventive subject matter is considered to include defining a training cohort based on attributes used to characterize a population from which sensor data will be obtained as training data.

The sensor data may be stored or otherwise retained for training in different ways. In some embodiments, once a cohort has been defined, the corresponding sensor data and known healthcare outcomes can be stored as raw data. In additional or other scenarios, the sensor data could comprise a reduced set of sensor data that focuses only on the necessary features for training. Still further, the sensor data can also include leading indicators derived from sensor data. However, it should be appreciated that leading indicators do not necessary represent actual indicators and may not be known a priori and might have to be discovered during training.

Continuing with method 300, step 320 comprises compiling known state training data. The known state training data can be considered the input to the training process. It is possible in some embodiments the known state training data is not yet organized as the leading indicator that may yet be discovered. In view the prediction agents need to make a prediction in the future, the known state training data may comprise a set of known states of individuals at specific points in time from the past through to when an action was taken. Therefore, the known states can be labeled with time information (e.g., snap shots, etc.) as well as sensed modality information (e.g., heart rate, temperature, etc.) as suggested by step 325. Further each state (e.g., a single snapshot, etc.) or each set of states (e.g., a time series of snapshots, etc.) can also be labeled with corresponding actions that were taken as indicated by step 327. For example, the corresponding actions can include a CPT, ICD, or DSM codes as suggested previously or can include other actions, including those that adhere to a well-defined namespace.

An example technique that may be adapted for use in identifying possible correlations between the sensor data, leading indicators, or input vectors and possible actions are described in U.S. Pat. No. 10,296,840 to Soon-Shiong titled "Reasoning Engine Services," filed Aug. 25, 2017. For example, the described techniques can be adapted by using the sensor data as a potential data space where the sensor data may be compiled into leading indicators that can be considered data objects. Via use of one or more reasoning rule sets, a training computer system may establish potential correlations with known outcomes (e.g., CPT codes, ICD codes, etc.). The result of the reasoning analysis can include one or more hypothesis, which can represent how the leading indicators may relate to the outcomes. Such information may be automatically incorporated into the training data or presented to a stakeholder for selection, possibly via a training dashboard.

Step 326 further contemplates, the known states can be labeled as leading indicator states, if such leading indicator states are a priori known. Thus, step 326 provides for aggregated learning over time. As new data is compiled from the cohort, the leading indicators from the new data can be used to populate or increase the size of the training data set.

From a more detailed perspective, compiling the known state training data can also include populating one or more input vectors that may be used for the prediction agents to be trained. The input vectors may already be defined (i.e., a type of leading indicator) or yet to be discovered. Therefore, one aspect of the inventive subject matter is considered to include, although optional, varying the nature of the input vectors, in conjunction with the nature of the prediction agents as discussed below. Still, variation of the input vectors can be according to one or more established rules by which input vectors are established for the training process.

Several approaches can be used to vary the definition of the input vectors. In some embodiments, genetic algorithms can be used to cause the input vectors to vary. For example, the number of temporal snapshots can be varied (e.g., retain 1, 2, 3, 4, or more snapshots, etc.), the data modalities can be varied, or the demographic information could be varied just to name a few. The advantage of such an approach is the training computer system can discover which sensor data makes the largest impact on correctly predicting the corresponding outcomes. Still, in less preferred embodiments, the training computer system could simply use a brute force approach of trying as many different input vector definitions based on a finite list of parameters as possible according to a set of defined input vector rules to determine which works best.

As discussed previously, the leading indicators and hence the input vectors might actually comprise more than one data modality in combination. To determine such occurrences the method can further include conducting one or more principle component analyses to identify which features, in combination, aid in driving the specific action outcome. The main thrust behind varying the input vector is to discover which leading indicators may be strongly coupled with the known outcomes (i.e., that actual actions taken in the training data sets).

Still further, the known states can be analyzed via machine learning clustering to identify clusters that could be bound to a known outcome action. For example, the known states (e.g., sensor data, input vectors or its members, leading indicators, etc.) would typically fall within a high dimensional space. Example implementations of clustering algorithms include affinity propagation, k-means clustering, BIRCH clustering, or other known clustering algorithms. These algorithms and others can be obtained via Scikit-Learn (see URL scikit-learn.org). The advantage of such an approach is each cluster can be considered indicative of a set of leading indicators that can be directly linked with a known action. Thus, a trained prediction agent using clustering can quickly identify when test data falls close to or within such a cluster.

One should appreciate the compiled known state training data can be encoded according to different schemes. In some embodiments, the data could be represented in RAM as text-based states: "Walking," "Running," or "Stationary" for example. Corresponding input vectors might include members that have a binary representation if such states are active. A bit representing the state of "Walking" might be 0 (inactive) or 1 (active) for example. Alternatively, the corresponding members might have an integer or floating-point value indicating the confidence of detecting the state: Walking-0.8, Running-0.2, Stationary-0.1 for example. Still, as can be appreciated, the encoding scheme depends on the nature of the training data set and the corresponding prediction action agent to be trained.

Step 330 includes instantiating one or more action prediction agent in the memory of the training computer system. While step 320 is illustrated as occurring after step 320, one should appreciate in may be done in parallel or in series with step 320. For example, as input vectors are varied, the instantiated action prediction agent can be changed to accept the new input vector. The opposite could also be true where changes to the architecture prediction agent may require changes to the input vector. In more preferred embodiments, the changes are made at the same time to ensure consistency and synchronicity between the two data structures.

Action prediction agents can be instantiated in memory based via calls to an appropriate library of implementations of corresponding machine learning algorithms. Example machine learning models can include neural networks (e.g., CNN, RNN, LS™ models, etc.) as suggested by step 335, support vector machines, clustering algorithms, classifiers, regression models, or other types of models. Although a single prediction agent may be found useful, it is also contemplated that an ensemble of prediction agents can be instantiated as suggested by step 337. Having an ensemble provides for reducing bias that may be found in single, individual models.

Of particular note, once trained, the action prediction agents will typically be deployed in embedded devices (e.g., cell phones, device servers, dedicated devices, etc.) with limited memory or computational power. Therefore, trained action agents having reduced memory foot prints or necessary computational power are more preferred over more bloated training action prediction agents.

Turning toward step 340, method 300 includes training an instantiated action prediction agent. Training also can take on many different forms and depends on the nature of the agent. More specifically training may vary depending on which implementation of a machine learning model is used (e.g., NN, classifier, regression model, LS™ model, etc.). As discussed previously, training may include training the models on domain or context specific data associated with a cohort. In some embodiments, training can include training many different models in parallel on a model training computer system infrastructure to determine which trained ensembles of models are most fit for use. Typically, each model is trained according to a fitness function which is a measure of how well the model is able to make predictions on training data. For example, training can include using a cross-fold validation schema where some portion, typically about 80%, of the data is used for training while the remaining portion, about 20%, of the data can be used for testing the predictions.

One should appreciate the fitness function does not necessarily have to yield perfect results. Rather, in some embodiments, the fitness function can measure when training is "good enough," especially in different contexts. For example, for an athletic domain with a focus on dehydration, the fitness function might indicate that 70% accuracy is good enough because taking the predicted action (e.g., drinking water, etc.) does no significant harm but has a major impact on the health of the athlete. However, in a case where the domain is related to care in a hospital, the fitness function might have a much higher accuracy requirement, say 95% or even higher, to ensure the predicted actions are indeed appropriate. While fitness functions can be defined based on the models or needs of the domain, typical fitness functions can use area under a receiver operator characteristic curve (AUC ROC), sigmoid functions, or other types of functions.

A fitness function does not necessarily have to depend on accuracy alone. In some embodiments, a fitness function can be defined based on the target use-case or even target device. Thus, factors including time to make a prediction, memory foot print, latency, or other attributes related to the use-case may be used. For example, a trained prediction agent might be required to consume no more than 1 MB of RAM and make a prediction in less than 10 ms. Thus, the fitness function would have these constraints and the model having the highest accuracy within these constraints may be selected. Therefore, a fitness function can represent fitness criteria defined based on the domain or context specific use cases.

Part of the training process can also include varying the action prediction agent architecture (i.e., the architecture of the model to be trained) as indicated by step 345. In some embodiments, the input vector for the altered model does not change to ensure the system does not necessarily have to repeat step 320. However, it is also contemplated that variations of the model's architecture could be performed in conjunction with repeating steps 320 or 330 as necessary. Varying the architecture provides the advantage of finding or discovering an architecture that provides for best accuracy while also servicing the domain or context specific requirements (e.g., low latency, low memory footprint, reduce processor use, energy consumption, lower heat generation, longer battery life, etc.).

The architecture of an action prediction agent can be varied automatically. One example of automatically varying the architecture includes using a genetic algorithm (see step 346) by which layers, nodes, or other features are added or subtracted from an initial model. Not only can the system discover the best architecture giving the model selection criteria, but acceptable modes that are "good enough" can also be incorporated into a desired ensemble of models. An example genetic algorithm that may be used in conjunction with neural networks includes NeuroEvolution of Augmenting Topologies (NEAT; see URL en.wikipedia.org/wiki/Neuroevolution_of_augmenting_topologies). NEAT provides for altering the weights and/or the structure of the network according to a genetic algorithm that may be used to achieve a NN having the desired characteristics (e.g., footprint, speed, accuracy, etc.).

Training of the action prediction agents can be interactive or automatic. As training continues, the results of the fitness function can be displayed on a dashboard (e.g., web page, etc.) for the training system. In embodiments where thousands or millions of models are being trained at the same time, a dashboard may only display a current status while the system automatically trains the models of the action prediction agents. Thus, at step 350, the fitness function can be tested and based on the fitness function failing to satisfy fitness criteria, training can continue with new parameters. Otherwise, the trained action prediction agent can be stored at step 360.

Storing a trained action prediction agent, step 360, may typically include storing the parameters of the trained agent in the memory of the training computer system. Further, storing a trained action prediction agent may include packaging the trained agent, alone or as a member of an ensemble, in a package for installation on a target sensor hub (e.g., device server, cell phone, dedicated device, etc.). Such a package can include creating a containerized version (e.g., Docker, Kubernetes, etc.) of the agent capable of running on a target platform (e.g., Linux, Windows, Android, IOS, etc.). Such packages can include additional features beyond the trained prediction agent including rules for converting target sensor data into leading indicators and ultimately into input vectors tailored toward the trained agent, rules for registering one or more listeners that observe the sensor data to determine when the trained prediction agent should be considered active, rules for converting the predicted actions from the trained action prediction agent into notifications or alerts, rules governing routing notifications or alerts to target stakeholders, or other useful features. Example techniques suitable for routing notifications that may be adapted for use with the inventive subject matter includes those described in U.S. Pat. No. 11,017,884 to Soon-Shiong titled "Discovery Routing Systems and Engines," filed Jun. 24, 2019.

Figure 4:
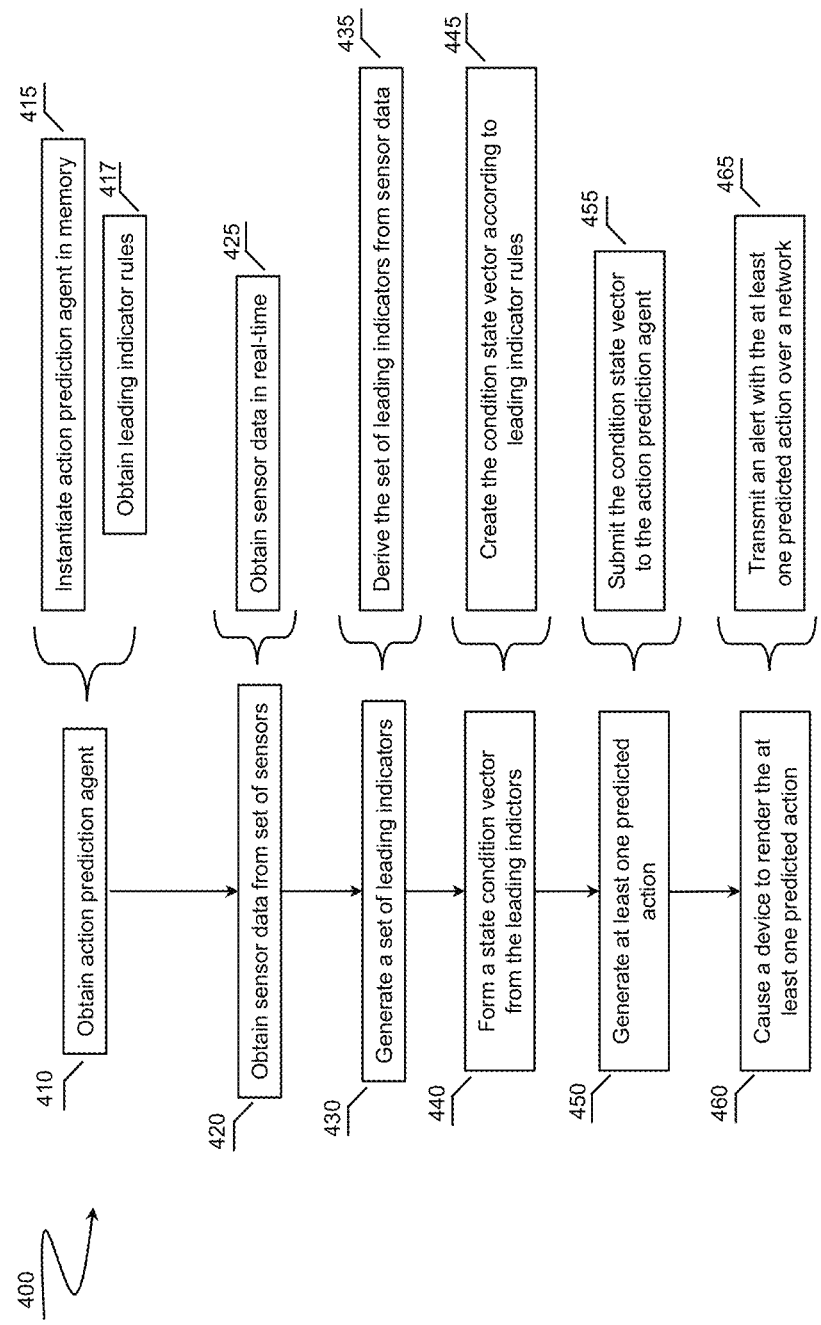
FIG. 4 illustrates a method of using a trained action prediction agent to generate one or more predicted actions based on observed leading indicators in sensor data collected over a PAN.

FIG. 4 presents computer-based method 400 of using a trained action prediction agent based on "in the field" inference data. Beginning with step 410, method 400 includes obtaining a trained action prediction agent. Obtaining a trained action prediction agent may depend on the nature of a target use case. Typically, the trained action prediction may be installed on a target computing device (e.g., cell phone, sensor hub, device server, appliance, medical equipment, computer, etc.), possibly as an application. In more preferred embodiments, the trained action prediction agent is a member of a software package, which could operate as a subscription-based package, personalized application, context or domain-specific applications, or other type of package. Further, as discussed previously, such packages may be provisioned with corresponding rules by which the trained action prediction agent services should operate.

While some embodiments focus on installing the action prediction agent on a local device proximate to the target individual, it should be appreciated that an action prediction agent may be deployed on a remote device, possibly operating as a remote service on a cloud-based system. In such cases, the sensor hub obtaining sensor data related to the individual may package the sensor data, leading indicators, or input vectors into one or more data packets and transmit them over a network to the remote prediction service. Such an approach is advantageous when a local device lacks sufficient resources to run the action prediction agent, or where network communication latency is not an issue.

In view that an action prediction agent may be context specific, in some embodiments the action prediction agent may be instantiated as suggested by step 415 as a context associated with the individual changes with time. For example, one or more context listeners within the prediction device may observe the sensor data, leading indicators, or even the input vectors of the action prediction agent over time. When a context listener's context criteria are satisfied by the observations, the context listener can instantiate a corresponding action prediction agent in the prediction device's memory. The reverse may also be true. When a context listener's context criteria are no longer satisfied, the action prediction agent may be removed from the memory via calling an appropriate deconstruct method. For example, a context might be defined by various environmental attributes, time attributes, sensor data, individual attributes, or other information. Perhaps location may be used to determine if the individual is on a sports field or in a hospital, which then may be used for a sports-based action prediction agent versus a critical care-based action prediction agent. Further, acceleration or geolocation information could be used to distinguish between an action prediction agent for a sedentary individual versus an action prediction agent for an active individual that is outdoors. Still in other cases, the action prediction agent could be purpose built for a specific use case and can be a priori generated in a device or its memory. For example, in professional athletics it is expected that certified devices and/or equipment would have an approved action prediction agent pre-installed on the certified equipment before professional matches begin. Therefore, one aspect of the inventive subject matter is considered to include certifying an action prediction agent, its corresponding package (e.g., leading indicators, input vectors, etc.), or the target prediction device or hardware.

There are also additional optimizations that can be employed with the inventive subject matter based on contexts or domains. As discussed above, a context can be sensed based on the flow of sensor data (e.g., time, location, gate, speed, elevation, etc.). Still, not all sensor data may be necessary for given context or domain specific use case. In which case, as a new context is sensed, the sensor hub can reconfigure the sensors in the individual's PAN to behave in an appropriate manner suitable to the new context. For example, some sensors may be turned on, other sensors may be turned off, sensors may be instructed to increase sensing rate, sensors may be instructed to decrease sensing rate, or otherwise have their operations modified. Example techniques that may be leveraged for reconfiguring sensors are described in U.S. Pat. No. 10,762,171 to Dyell et al. titled "Patient Sensor Data Exchange Systems and Methods," filed Sep. 5, 2019. For example, as a context of the individual changes, a request can be sent to the sensor hub or sensors to reconfigure the sensors to be responsive to the new context.

The action prediction agent may also be coupled with one or more rules by which the leading indicators are compiled. Thus, as indicated by step 417, the method can further include obtaining such leading indicator rules. The leading indicator rules may be implemented as compiled executable code, a script (e.g., LUA, Python, Java, etc.), a markup-language file (e.g., JSON, XML, YAML, etc.), or other computer readable instructions. In view the leading indicators may be associated with a context-specific action prediction agent, the corresponding context-specific leading indicators may also be context specific. Therefore, as context changes, the leading indicators could shift from single valued, direct mappings from the sensor data to multi-valued indirect mappings of the sensor data or other types of derived values from the sensor data. An example where the leading indicators might change while the sensor data remains the same includes using a ratio of heart rate to movement (e.g., rate of movement, speed, etc.). For a sedentary individual (i.e., movement is zero), the ratio might not make sense as a leading indicator. Rather, a sedentary leading indicator might just use heart rate. However, for an active individual, the ratio may make sense and be a valid leading indicator. In these two cases, the exact same sensor data may be used to generate two completely different context-based leading indicators.

Turning toward step 420, the method further includes obtaining sensor data from one or more sensors, which may be obtained in real-time as suggested by step 425. In some embodiments, the sensor data may be transmitted over a network to a device where the action prediction agent is installed. Still, the sensor data may be locally processed by sensor hub located proximate to the individual, possibly within a PAN. The sensor data may be obtained by the sensor hub as one or more data streams, possibly representing waveforms such as EKG, as one or more discrete values (e.g., temperature, time stamp, location, etc.), or other forms. The sensor data may be obtained in a raw format which might require conversion to a useable unit of measure. For example, a piezoelectric sensor might report a value between 0 and 255, which then can be converted to the appropriate units (e.g., pressure, force, weight, etc.). In addition to or alternatively, the raw sensor data may be converted through other techniques as well, possibly via a software implementation of a function, a look-up table, a machine learning transform, or other technique.

Step 430 includes the computer system generating one or more sets of leading indicators, typically from rules included with corresponding prediction agents. More specifically, the leading indicators can be derived directly or indirectly from the sensor data, possibly in real-time as indicated by step 435. Still, it should be appreciated the leading indicators can also include information beyond just the sensor data itself. For example, in addition to using just the sensor data, the leading indicators might leverage information about the environment (e.g., locations, time, weather, barometric pressure, etc.), the individual under observation (e.g., age, gender, diet, demographic, etc.), or other ambient information. Such information can be leveraged to add color to the nature of the raw sensor data via the leading indicator rules. With respect to real-time generation of leading indicators (step 435), one should appreciate that the nature of real-time can vary depending on the nature of the corresponding sensor data. In some embodiments, the leading indicators may be generated periodically on a regular basis as the sensor data flows into the sensor hub (e.g., every 1 ms, 5 ms, 10 ms, 1 s, 10 s, 1 minute, 1 hour, etc.). Still further, the leading indicators may be generated in real-time irregularly, possibly only when changes to the sensor data are detected. For example, a body temperature might not change very rapidly and therefore, corresponding leading indicators may need to be generated or updated only when the change in body temperature is detected. Thus, real-time generation of leading indicators can be adjusted or established as necessary based on the sensor data. The approach of abstracting the sensor data from the leading indicators provides the technical advantage of only invoking the prediction agent when necessary rather than having a prediction agent run continuously, thereby conserving computational resources for additional prediction agents to run in parallel.

While the leading indicators could be generated all at once or separately, they may also be packaged for transmission to a remote sensor hub (e.g., a cloud-based analysis computer, etc.). In such scenarios, the leading indicators can be collected as a single data package (e.g., XML file, JSON file, binary encoded packet, etc.). Still further, or in addition to, the leading indicators may be packaged using different techniques as well including providing streams of data, collectively or individually. For example, one or more TCP/IP data streams may be established from a local sensor hub to a remote analysis system for each prediction agent or for each type of leading indicator. The streams can present the leading indicator data (or even the raw sensor data) continuously, periodically, as needed with a timestamp, or according to the other timing as desired or necessitated by the system (e.g., synchronously, asynchronously, isochronously, etc.). In view the system is designed to forecast or otherwise make time-based predictions, in more preferred embodiments, the leading indicators are generated and tagged with timestamp information, or even other types of metadata (e.g., location, etc.).

At step 440 the generated set of leading indicators are formed into one or more state condition vectors, where a state condition vector comprises a data structure as input into the trained action prediction agents. Further, state condition vector represented a general condition or state of the individual at a point-in-time or points-in-time. Depending on the needs of the action prediction agent, the condition state vector may be formed according to various requirements. In some scenarios, the condition state vector may be represented as a one-dimensional vector where each member of the vector represents a value or state. In more sophisticated embodiments, the condition state vector can be represented as a multi-dimensional vector. For example, the vector could be formed as a two-dimensional vector where one dimension represents a time dimension. More specifically, the condition state vector could comprise a set of values or inputs at different times: $t_{-N}, \ldots, t_{-2}, t_{-1}, t$. where $t$ is a current timestamp and the numeral subscripts represents previous timestamps. For example, the sets of value could be formed for the current time ($t$), a previous minute ago ($t_{-1}$), a previous two minutes ago ($t_{-2}$), and so on. One should appreciate the use of minutes is presented as an example; other time periods regular or irregular may be used. Thus, in such embodiments, the condition state vector can be considered a time-based stack of data structures. Creating such time-based condition state vectors allows the action prediction agent to forecast or make predictions based on observed temporal features or trends.

In view action prediction agents may make predictions for domain or context specific circumstances, one should appreciate that the condition state vectors can be created according to leading indicator specific rules corresponding to the domain or context specific circumstance as suggested by step 445. In such cases, when the sensor hub, or other device, installs a prediction package, the package can also include rules or other software instructions that govern how leading indicators can be formed into the specific condition state vector for the corresponding action prediction agent. Interestingly, this approach provides several advantages. First, as discussed previously, the same leading indicators can give rise to different condition state vectors to be used for different purposes. Second, the same condition state vector could be used for different action prediction agents. For example, two action prediction agents may be trained on different data yet have the same input requirements, which can aid in reducing bias by having different agents generate different (or the same) actions.

Recall the action prediction agent comprises one or more trained machine learning or deep learning models and are deployed in a computer device. Thus, at step 450, the device or devices can take the step of generating at least one predicted action. Typically, in most embodiments, the action prediction agent receives a submitted condition state vector as indicated by step 455. For example, the action prediction agent may receive the submitted condition state vector via an API call, a shared memory location, via wired or wireless interface, or even receive the submitted condition state vector over a network connection.

One should appreciate that submitting the condition state vector does not necessarily comprise a one and done (one-time) action. Rather, in some embodiments, step 455 may be a continuous action in the sense that as time passes the condition state vector is updated and submitted again to generate one or more new predicted actions. Submission of the condition state vector could happen at periodic intervals (e.g., every 10 ms, every second, every 2 seconds, every minute, etc.), based on triggered events (e.g., when a new state is detected, when a new context is detected, etc.), submitted only when the condition state vector changes, or according to other timing requirements that may be encoded with the context or domain specific prediction package.

Yet another interesting point is the nature of the action prediction agent. In the in the context of deep or machine learning, especially in models leveraging classifiers, the results from the action prediction agent could comprise more than one predicted action. In fact, in many scenarios, the output of the action prediction agent or agents comprises a set of predicted actions, possibly ranked according to likelihoods (e.g., scores, metrics, normalized probabilities, etc.).

Recall the disclosed system processes leading indicators as time series data. Therefore, predicted actions can also comprises time series data. For example, the output could comprise a one-dimensional list of predicted actions ranked by their likelihoods, where list changes with time or is updated as time flows.

The time series output can also be converted to one or more "action waveforms," which can be considered a form of visualization showing likelihood of the various actions or show how the predicted actions may change with time. Thus, the action waveforms can provide a history of the rise and/or fall of predicted actions as a function of time similar to EKGs or other types of waveforms. Further, the predicted action list along with each action's probability could also become a form of leading indicator which may be fed back into the prediction agent. Naturally, the action prediction agent must be a priori built for such an input signal and appropriately trained.

The predicted action can take on different forms. In some scenarios the action or actions can comprise CPT codes or even suggested IDC codes for the recommended actions. Additional information can be used to create a more holistic recommended action plan beyond actions to take by chaining additional actions together stemming from one or more initial predicted action. In addition, the action plan can include a predicted point of care, predicted location of care, predicted moment of care, recommended care giver, predicted time of care, or other information.

While the prediction agent can generate a predicted action, the overarching system may be programmed to understand that a predicted action might not be serviceable at the predicted time. For example, a hiker in the woods might have leading indicators of exhaustion or dehydration. However, the hiker could be remote relative to locations that could provide the predicted actions, say remote from a safe resting place and/or safe drinking water or intravenous (IV) drip. In such cases the predicted action can be coupled with the ancillary information (e.g., location, context, etc.) to create a more complex set of instructions that may chain together to provide necessary care.

While services might not be immediately available at the predicted point of care or a location of care, the predicted actions can be further analyzed by a chaining rules engine that may be able to create a chain of actions to provide services to the individual. Returning to the hiker example, the system can recognize based on context that a hiker can not be reached by the predicted time-of-care. In which case, the rules can dictate additional actions to give rise to the opportunity to provide additional recommended services; call 911, have a drone drop water, prepare a rescue, or other actions. Still further, if the predicted action cannot be given, the predicted action can be updated based on an escalation set of rules. If the leading indicators indicate dehydration is likely to occur, but no IV can be given and also the individual cannot be taken care of quickly, their condition might worsen. In which case, care might include hospitalization or other more extreme actions may be generated due to the time lag between when the original action was predicted and when care can be practically provided. Therefore, a predicted action may be part of an action plan that could include an escalated action that might be more severe than providing initial care.

At step 460, the method can include causing an output device to render the predicted action. The action prediction agent can compile the predicted action along with other information as a message, which can be transmitted over a network (step 465) if necessary. For example, the message can comprise a JSON, XML, YAML, or other type of markup language along with optional metadata. In addition to or alternatively, the message can also comprise binary digital data, perhaps including image data, location data, raw sensor data, or other information that a care provider might want or require. In more preferred embodiments, the rendered prediction agent comprises information that adheres to one or more standard or well-defined encoding schemes to ensure uniformity of care. Example techniques that may be adapted for routing predicted action information to one or more stakeholders is described in U.S. Pat. No. 11,017,884 to Soon-Shiong titled "Discovery Routing Systems and Engines," filed Jun. 24, 2019. For example, predicted actions may be generated based on a discovery of anomalous behavior of the individual. In which case, the type of action may be mapped to a stakeholder via a look up table or possibly based on which stakeholders subscribe to the individual or to specific actions.

To provide a better understanding of the inventive subject matter, consider an example where the predicted action comprises a recommendation of providing cardiopulmonary resuscitation (CPR) for an individual whose leading indicators suggest that they might be expected to suffer heart failure. The message supporting the predicted action can be compiled along with supporting information and associated metadata. For example, the predicted action message could include a CPT code of 92950 (i.e., the CPT code for CPR at the time of this writing). While such information might be useful to a skilled physician, such detail might be lost on a non-skilled provider. If the predicted time-of-care and predict point-of-care is such that only non-skilled providers are proximate to the individual, the message can further include one or more video instructions on how to conduct CPR to walk the non-skilled care provider through the procedure. Still, the message can include a complete set of information (e.g., CPT codes, video instructions, contact information, chained instructions or actions, etc.) or just partial information that best fits with the target provider. Thus, one aspect of the inventive subject matter is considered to include rendering a predicted action that is aligned with the provider's skill set, the provider's knowledge, or the provider's context.

Beyond sending a notification comprising a predicted action or rendering a prediction action, one should appreciate additional actions can also be taken. In some embodiment, the various events that occur during deployment and use of action prediction agents may be archived for future use. Consider a scenario where the individual's medical records may require updates based on the observed events. The data may be stored in a medical record repository using known techniques. Especially interesting techniques include recording the events based on a Health Object Identifier (HOI) as described in U.S. Pat. No. 11,017,897 to Soon-Shiong titled "Healthcare Management Objects," filed Mar. 22, 2012. More specifically the event data can be stored using a patient identifier as a prefix for the data while the suffix might be leading indicators or predicted actions (e.g., outcomes, etc.). The archived event data can include a broad spectrum of information including timestamps, version numbers of the action prediction agents, raw sensor data snapshots, leading indicator snapshots, condition state vector snapshots, predicted actions, hypothesis on predictions (see U.S. Pat. No. 10,296,840), or other related information. The features of the event data may be archived individually, possibly as requested by a stakeholder, or collectively in any combination.

Another technique for archiving event data includes recording the event data either directly or indirectly via an address, identifier, reference, or other indexing scheme on a notarized ledger. Example notarized ledgers include blockchains (e.g., Ethereum, BitCoin, Solana, Ripple, etc.), hash graphs, distributed ledgers, semi-public ledgers, private ledgers, centralized ledgers, or other notarized ledgers where the data may be considered immutable or nearly immutable. Example techniques that may be leveraged for storing such event data includes those described in U.S. Pat. No. 10,340, 038 to Witchey titled "Healthcare Transaction Validation via Blockchain, Systems and Methods," filed May 13, 2015. Such approaches are advantageous because the event data can be considered validated data that may be used for future training of action prediction agents in a reproducible manner or that may be considered auditable, credible data for insurance purposes.

In view the disclosed system is based on predictions founded based on implementations of trained deep learning or machine learning algorithms, there is no guarantee that the predicted action would actually be performed or would be necessary at the predicted point-of-care. Therefore, the system can further track outcomes of the predictions, where the actual outcome can take on different forms. In some cases, the actual outcome might simply be "no action taken." However, the outcome "no action taken" could be further qualified as being unnecessary, unable to perform, incorrect, or other type of qualification, which may aid in reinforcement learning. Still, there will also be outcomes that are correct, which should also be tracked. Returning to the CPR example, an outcome of "action taken," would indicate that the predicted action was indeed correct and performed. Still, the "action taken," could also be qualified to indicate just the action was taken, or could be qualified along with other actions performed in addition to one or more of the predicted actions. The approach of tracking actions actually taken or not taken, especially at a point-of-care or time-of-care, provides for generating additional training data for the machine learning implementations in the inventive subject matter. Therefore, the action prediction agents or other aspects of the ecosystem can be updated using the new feedback to further update its models in order to account for newly learned information. Yet another aspect of the inventive subject matter includes continually or continuously updating the models based on actual outcome of predicted actions. Such updates can be performed periodically as sufficient new data warrants, at regular intervals, as regulations of preferred actions change, based on changes in standards of care, or other triggering events.

While the above discussion focuses mainly on providing healthcare, there are additional uses for the inventive subject matter. From an athletics perspective, individual athletes may be monitored during training or competitions. Such an approach provides for identifying problems with the athlete before they report the issue (e.g., injuries, pain, discomfort, etc.). Of particular interest, athletes might not wish to report an injury, which could lead to further harm if the issues are not addressed. Thus, coaches or caregivers can monitor the athlete to ensure the athlete remains in acceptable health or to become aware of an issue possibly even before the athlete is aware the issue. Such system can be incorporated in a PAN of the athlete so that devices may report on possible issues, perhaps including concussions, cramps, bleeding, pain, breaks, sprains, strain, or other problems.

Overlapping with healthcare, the military could also leverage the disclosed techniques. While the system could monitor soldiers in training or in battle, the system can also monitor groups of soldiers to determine when the group might need supporting aid beyond healthcare. As a troop of soldiers work toward accomplishing a mission, sensor data from individuals in the group may be aggregated to form a group set of leading indicators, which could indicate specific needs; logistics support, food, supplies, ammunition, rest, or other types of aid, including aid beyond healthcare.

Continuing from the perspective of managing groups or teams, the inventive subject matter could be used to managing care for non-humans. While the system may be used to monitor individual animals, the system can also be used to monitor herds or flocks of animals such as cows, sheep, chickens, geese, or other groups of animals. In such cases, each animal might be provisioned with an individual wireless sensor array the provides data to a sensor hub that aggregates the sensor data from the group. Leading indicators in such a use case would then relate to the group in general. For example, the accelerometer data could be used to determine if the herd moves in aggregate, possibly indicating a predator is nearby, indicating a migration toward a specific area at a feeding time, or indicating a need to get out of the sun.

While the above discussion specifically relates to predicted actions that may be rendered for a healthcare provider, it is also possible the predicted actions could also include machine or device instructions. Thus, rather than a CPT code or other similar type of code, the predicted action could comprise a call to an API (e.g., remote procedure call, web service, device-specific action, etc.) or other type of invocation of a machine action. Such actions may be useful when a care provider is unavailable, but equipment is available. If the individual is able, they may be able to engage the equipment where the equipment or other such device can take automatic actions.

Most of the above discussion relates to an individual that is active (e.g., athlete, nominally healthy person, etc.) that may be moving around a location, traveling, or otherwise engaging in physical activities. However, one should appreciate that the disclosed techniques can also be applied to more passive individuals. For example, the sensor data may represent a person that is sedentary, perhaps eating dinner and watching television. While such a person may not be physically active, their body is still generating a significant amount of information. In such cases, leading indicators might be narrowed to a set that focuses on heart rate, blood pressure, temperature, or other similar parameters that do not require physical exertion. Thus, the system may detect the sedentary individual is under stress (e.g., high heart rate, high blood pressure, etc.) and might generate a predicted action of "stop watching news" or "take blood pressure medication."

Along a similar vein, such a sedentary individual might also be a patient in a hospital that is already under care and under observation. In such cases, additional information may be incorporated with the sensor data to form the leading indicators. For example, previous actions taken with respect to the patient can be combined with active sensor data to arrive at leading indicators where the previous actions could comprise CPT codes, ICD codes, DSM codes, provided drugs, provided surgeries, relative times between previous actions, or other ancillary data related to the individual that may be relative before a current point in time. While such information might be "static" in nature, the information may have a relative life time or time of relevance. Thus, the ancillary information can be coupled with time information where the time information may be used as a weight (e.g., a down-weight, an up-weight, a decay, etc.) for the relevance of the ancillary information. Observing patients and generating predicted actions is considered advantageous because it provides for identify possible worsening conditions of the patient before the patient's condition becomes critical.

From a more specific perspective, consider Analytic for Hemodynamic Instability (AHI). Currently such systems, including those produced by FifthEye™, focus on detecting when hemodynamic instability occurs based on machine learning systems. However, such systems fail to predict that such instabilities are likely to occur. For example, FifthEye seeks to detect changes indicative of hemodynamic instability, but does not provide predicted actions to be taken before hemodynamic instability impacts the individual. The disclosed approach advances such technologies several fold. First, previously unknown leading indicators may be discovered through training prediction agents via varying the structure of the training data or varying the structures of the prediction agents. Second, the disclosed system may predict issues before they arise at all. Third, the disclosed system may generate predicted actions that can be preventative in nature or address needs of the individual before such a critical condition arises.

Still further the above discussion relates to identifying potential problems that may need to be addressed at a point of care or moment of care. However, the disclosed inventive subject matter has utility beyond providing healthcare actions at a future point. In fact, the disclosed subject matter may be used to predict when an individual, or group, will be at a point of peak performance or peak health. For example, returning to the athlete in training example, the athlete may be training for quite some time. Trained action prediction agents may generate one or more predicted actions that could include recommendations on when the athlete should compete. Thus, the prediction actions may include other types of actions beyond providing healthcare and could include recommended actions possibly including, when to rest, went to shift training, when to compete, where to eat a next meal, who to talk to about their current state (e.g., motivation, mental state, etc.), or other forms of non-healthcare related actions.

Returning to the concept of archiving event data on the notarized ledger, it is also contemplated the predicted actions and any desired associated data (e.g., sensor data, leading indicators, version numbers, condition state vectors, predicted actions, CPT codes, etc.) can be compiled into a digital token representing at least a portion of the corresponding event. One should appreciate the digital token may include the actual data or may indirectly reference the data (e.g., point to where the data is stored, identify the actual data, provide addresses to the data, URLs, etc.), which may be more preferred in some embodiments. More specifically, the digital token can be considered to represent the event or memorialize the event for later review or for use as a training data set. Digital tokens can then be "minted" as non-fungible tokens (NFTs) on a notarized ledger that may be created, burned, bought, traded, sold, or otherwise managed as distinct digital objects. There are multiple advantages of such an approach. For example, by representing an event or outcome as an NFT on a notarized ledger, the owner of the NFT (e.g., the individual, the sports team, etc.) may then monetize the NFT by selling the corresponding data to others, while also providing assurance the data is indeed valid (see also U.S. Pat. No. 10,340,038 referenced above). Additionally, through the use of NFTs and recording transactions related to the NFTs, the data may be audited at any time by interested parties. Still further, NFTs representing expected peak performance of athletes may memorialize greatness, perhaps winning a gold medal or other type of achievement. Such NFTs may become valuable in the market as a collectible. While each notarized ledger may leverage their own smart contract interfaces for managing digital tokens, an embodiment based on the Ethereum may leverage the ERC-721 interface for NFTs, ERC-1155 for collections of tokens, or even ERC-998 for composable tokens. Further, example techniques for leveraging NFTs as a proxy for a "right to access" healthcare data can be found in U.S. patent application Ser. No. 17/590,291 to Witchey et al. titled "Token-Based Digital Private Data Exchange Systems, Methods, and Apparatus," filed Feb. 1, 2022 (not yet published).

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 3 and 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
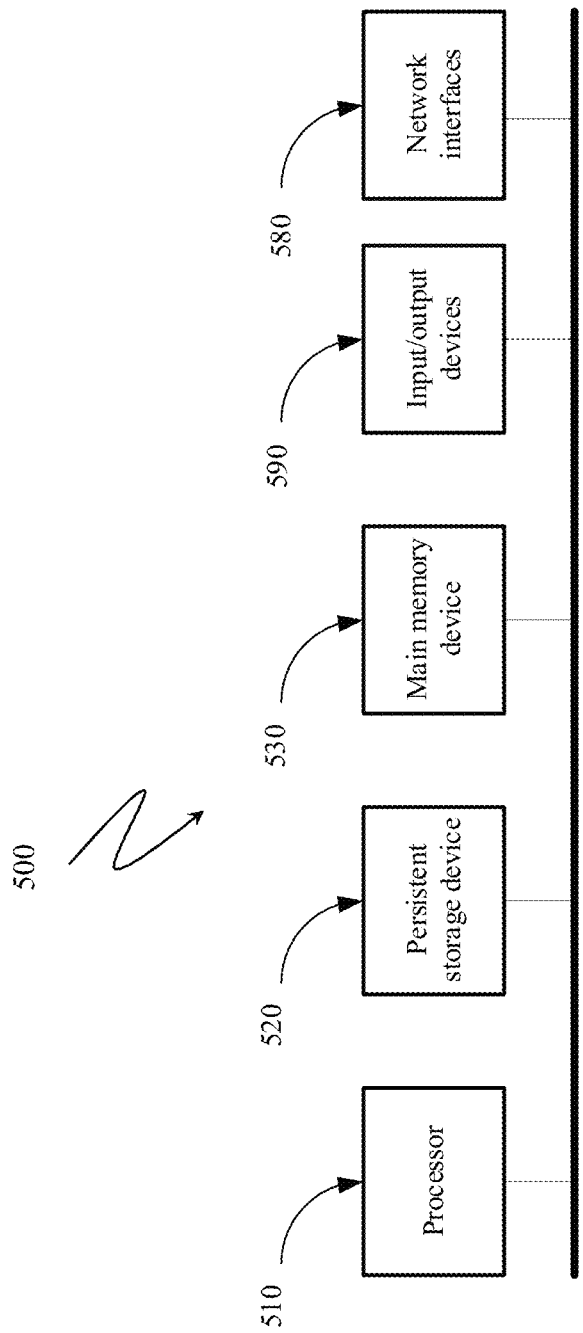
FIG. 5 illustrates a block diagram of a distributed computer system that can be used for implementing one or more aspects of the various embodiments.

A high-level block diagram of an exemplary apparatus that may be used to implement systems, apparatus and methods described herein is illustrated in FIG. 5. Apparatus 500 comprises a processor 510 operatively coupled to a persistent storage device 520 and a main memory device 530. Processor 510 controls the overall operation of apparatus 500 by executing computer program instructions that define such operations. The computer program instructions may be stored in persistent storage device 520, or other computer-readable medium, and loaded into main memory device 530 when execution of the computer program instructions is desired. For example, sensor hub(s) 120 and output device 165 may comprise one or more components of computer 500. Thus, the method steps of FIGS. 3 and 4 can be defined by the computer program instructions stored in main memory device 530 and/or persistent storage device 520 and controlled by processor 510 executing the computer program instructions. For example, the computer program instructions can be implemented as computer executable code programmed by one skilled in the art to perform an algorithm defined by the method steps of FIGS. 3 and 4. Accordingly, by executing the computer program instructions, the processor 510 executes an algorithm defined by the method steps of FIGS. 3 and 4. Apparatus 500 also includes one or more network interfaces 580 for communicating with other devices via a network. Apparatus 500 may also include one or more input/output devices 590 that enable user interaction with apparatus 500 (e.g., display, keyboard, mouse, speakers, buttons, etc.).

Processor 510 may include both general and special purpose microprocessors and may be the sole processor or one of multiple processors of apparatus 500. Processor 510 may comprise one or more central processing units (CPUs), and one or more graphics processing units (GPUs), which, for example, may work separately from and/or multi-task with one or more CPUs to accelerate processing, e.g., for various image processing applications described herein. Processor 510, persistent storage device 520, and/or main memory device 530 may include, be supplemented by, or incorporated in, one or more application-specific integrated circuits (ASICs) and/or one or more field programmable gate arrays (FPGAs).

Persistent storage device 520 and main memory device 530 each comprise a tangible non-transitory computer readable storage medium. Persistent storage device 520, and main memory device 530, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 590 may include peripherals, such as a printer, scanner, display screen, etc. For example, input/output devices 590 may include a display device such as a cathode ray tube (CRT), plasma or liquid crystal display (LCD) monitor for displaying information (e.g., a DNA accessibility prediction result) to a user, a keyboard, and a pointing device such as a mouse or a trackball by which the user can provide input to apparatus 500.

Any or all of the systems and apparatuses discussed herein, including sensor hub(s) 120 and output device 165 may be performed by, and/or incorporated in, an apparatus such as apparatus 500. Further, apparatus 500 may utilize one or more neural networks or other deep-learning techniques to perform sensor hub(s) 120 and output device 165 or other systems or apparatuses discussed herein.

One skilled in the art will recognize that an implementation of an actual computer or computer system may have other structures and may contain other components as well, and that FIG. 5 is a high-level representation of some of the components of such a computer for illustrative purposes.

The discussion herein provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

In some embodiments, the numbers expressing quantities of ingredients, properties such as concentration, reaction conditions, and so forth, used to describe and claim certain embodiments of the inventive subject matter are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the inventive subject matter are approximations, the numerical values set forth in the specific examples are reported as precisely as practicable. The numerical values presented in some embodiments of the inventive subject matter may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the inventive subject matter and does not pose a limitation on the scope of the inventive subject matter otherwise claimed. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A personal area sensor system comprising:
a set of sensors capable of capturing sensor data associated with an individual; and
a sensor hub communicatively coupled with the set of sensors and comprising at least one computer readable memory and at least one processor that, upon execution of software instructions stored in the memory, performs operations to:
obtain, in the memory, at least one action prediction agent configured to generate a predicted required action based on at least one condition state related to the individual;
determine a use case package related to the individual, the use case package comprising one or more executable code and data structure compilations, and one or more leading indicator rule sets corresponding to the use case;
generate, using at least one of the one or more executable code and data structure compilations in real-time, a set of leading indicators from the sensor data based on a context of the individual and according to the one or more leading indicator rules sets, the at least one of the one or more executable code and data structure compilations operative to convert the set of leading indicators into;
a condition state vector;
generate at least one predicted required action for a condition via the at least one action prediction agent based on the condition state vector relative to at least one known state related to the individual; and
cause, via transmitting an alert over a network, a computing device to render the predicted required action on an output of the computing device.

2. The personal area sensor system of claim 1, wherein the condition state vector comprises a time-based condition state vector.

3. The personal area sensor system of claim 1, wherein the at least one known state comprises a nominal state.

4. The personal area sensor system of claim 3, wherein the nominal state comprises a time-based nominal state.

5. The personal area sensor system of claim 1, wherein the set of sensors comprise at least two different sensors.

6. The personal area sensor system of claim 1, wherein the sensor data comprises at least two different data modalities.

7. The personal area sensor system of claim 1, wherein the set of leading indicators comprises imputed values from the sensor data.

8. The personal area sensor system of claim 1, wherein the at least one predicted required action comprises a predicted location of care.

9. The personal area sensor system of claim 1, wherein the at least one predicted required action comprises at least one of the following: a predicted time and a predicted urgency.

10. The personal area sensor system of claim 1, wherein the at least one predicted required action comprises a predicted treatment.

11. The personal area sensor system of claim 10, wherein the predicted treatment comprises a CPT code.

12. The personal area sensor system of claim 10, wherein the predicted treatment comprises a preauthorized treatment.

13. The personal area sensor system of claim 1, wherein the required action comprises at least one ICD code.

14. The personal area sensor system of claim 1, wherein the hub comprises a mobile phone.

15. The personal area sensor system of claim 1, wherein the hub comprises at least one of the following: a dedicated device, a vehicle, a smart watch, a smart card, and a set of electronic glasses.

16. The personal area sensor system of claim 1, wherein the hub further comprises a wireless interface over which the alert is transmitted.

17. The personal area sensor system of claim 16, wherein the wireless interface comprises at least one of the following: an 802.11 interface, a Bluetooth™ interface, a WiFi interface, a cellular interface, an IRDA interface, a 3G interface, a 4G interface, a 5G interface, and an NFC interface.

18. The personal area sensor system of claim 16, wherein the at least one prediction agent is obtained over the wireless interface.

19. The personal area sensor system of claim 1, wherein the at least one prediction agent comprises an implementation of a classifier.

20. The personal area sensor system of claim 1, wherein the at least one prediction agent comprises an implementation of a regression model.

21. The personal area sensor system of claim 1, wherein the at least one prediction agent comprises a trained neural network.

22. The personal area sensor system of claim 1, wherein the at least one prediction agent is customized to the individual.

23. The personal area sensor system of claim 22, wherein the customized based on at least one attribute of the individual.

24. The personal area sensor system of claim 1, wherein the operation of transmitting includes directing the alert to at least one specific stakeholder.

25. The personal area sensor system of claim 24, wherein the at least one specific stakeholder comprises an expert system.

26. The personal area sensor system of claim 25, wherein the operation of transmitting includes directing the alert to a specific group of stakeholders.

27. The personal area sensor system of claim 1, wherein the set of leading indicators comprises a multimodal vector derived from the sensor data.

28. The personal area sensor system of claim 1, wherein the set of leading indicators comprises values derived from the sensor data.

29. The personal area sensor system of claim 28, wherein the derived values comprise at least one derivative of the sensor data of at least 2nd order.

30. The personal area sensor system of claim 29, wherein the at least one derivative comprises a time-based derivative.

31. The personal area sensor system of claim 1, wherein the condition comprises a heath condition.

32. The personal area sensor system of claim 1, wherein the condition comprises a data collection condition.

33. The personal area sensor system of claim 1, wherein the at least one predicted required action comprises a passive action.

34. The personal area sensor system of claim 1, wherein the at least one prediction required action comprises an active action.

35. The personal area sensor system of claim 1, wherein the set of sensors comprises at least one of the following of the following sensors: a pulse-ox sensor, a heartrate sensor, a piezoelectric sensor, a thermometer, a galvanometer, a location sensor, a magnetometer, an EKG, an EEG, a blood pressure sensor, an accelerometer, a proximity sensor, an infrared sensor, a pressure sensor, a light sensor, an ultrasound sensor, a microphone, a camera, a particle detector, a flow sensor, a color sensor, LIDAR, a humidity sensor, a gyroscope sensor, a tilt sensor, and a touch sensor.

36. A computerized method comprising:
- obtaining, by a sensor hub communicatively coupled with a set of sensors, sensor data captured by the set of sensors and associated with an individual;
- obtaining, by the sensor hub from a memory, at least one action prediction agent configured to generate a predicted required action based on at least one condition state related to the individual;
- determining, by the sensor hub, a use case package related to the individual, the use case package comprising one or more executable code and data structure compilations, and one or more leading indicator rule sets corresponding to the use case;
- generating, by the sensor hub using at least one of the one or more executable code and data structure compilations in real-time, a set of leading indicators from the sensor data based on a context of the individual and according to the one or more leading indicator rules sets, the at least one of the one or more executable code and data structure compilations operative to convert the set of leading indicators into;
- a condition state vector;
- generating, by the sensor hub, at least one predicted required action for a condition via the at least one action prediction agent based on the condition state vector relative to at least one known state related to the individual; and
- causing, by the sensor hub transmitting an alert over a network, a computing device to take an action based on the at least one predicted required action, including rendering the at least one predicted required action on an output of the computing device.

37. A non-transitory computer-readable medium having computer instructions stored thereon, which, when executed by a processor, cause the processor to:
- obtain, by a sensor hub communicatively coupled with a set of sensors, sensor data captured by the set of sensors and associated with an individual;
- obtain, by the sensor hub from a memory, at least one action prediction agent configured to generate a predicted required action based on at least one condition state related to the individual;
- determine, by the sensor hub, a use case package related to the individual, the use case package comprising one or more executable code and data structure compilations, and one or more leading indicator rule sets corresponding to the use case;
- generate, by the sensor hub using at least one of the one or more executable code and data structure compilations in real-time, a set of leading indicators from the sensor data based on a context of the individual and according to the one or more leading indicator rules sets, the at least one of the one or more executable code and data structure compilations operative to convert the set of leading indicators into;
- a condition state vector;
- generate, by the sensor hub, at least one predicted required action for a condition via the at least one action prediction agent based on the condition state vector relative to at least one known state related to the individual; and
- cause, by the sensor hub transmitting an alert over a network, a computing device to take an action based on the at least one predicted required action, including rendering the at least one predicted required action on an output of the computing device.

* * * * *